(12) United States Patent
Germain et al.

(10) Patent No.: US 11,471,410 B2
(45) Date of Patent: *Oct. 18, 2022

(54) PHARMACEUTICAL COMPOSITION COMBINING AT LEAST TWO DISTINCT NANOPARTICLES AND A PHARMACEUTICAL COMPOUND, PREPARATION AND USES THEREOF

(71) Applicant: CURADIGM SAS, Paris (FR)

(72) Inventors: Matthieu Germain, Champigny sur Marne (FR); Marie-Edith Meyre, Saint Mande (FR); Agnès Pottier, Paris (FR); Laurent Levy, Paris (FR)

(73) Assignee: CURADIGM SAS, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 16/550,342

(22) Filed: Aug. 26, 2019

(65) Prior Publication Data

US 2019/0374465 A1 Dec. 12, 2019

Related U.S. Application Data

(63) Continuation of application No. 15/529,101, filed as application No. PCT/EP2015/077446 on Nov. 24, 2015, now Pat. No. 10,391,058.

(30) Foreign Application Priority Data

Nov. 25, 2014 (EP) .................................. 14306874

(51) Int. Cl.
| | | |
|---|---|---|
| *A61K 9/127* | (2006.01) | |
| *A61K 9/00* | (2006.01) | |
| *A61K 31/704* | (2006.01) | |

(52) U.S. Cl.
CPC ................ *A61K 9/127* (2013.01); *A61K 9/00* (2013.01); *A61K 31/704* (2013.01);
(Continued)

(58) Field of Classification Search
CPC ...................................................... A61K 9/127
See application file for complete search history.

(56) References Cited

U.S. PATENT DOCUMENTS

| | | |
|---|---|---|
| 4,280,918 A | 7/1981 | Homola et al. |
| 6,160,006 A | 12/2000 | Edwards et al. |
| (Continued) | | |

FOREIGN PATENT DOCUMENTS

| | | |
|---|---|---|
| CN | 102532154 | 7/2012 |
| EP | 2 000 150 | 12/2008 |
| (Continued) | | |

OTHER PUBLICATIONS

Robert M. Abra, Mark E. Bosworth and C. Anthony Hunt. "Liposome Disposition In Vivo: Effects of Pre-Dosing With Liposomes." Research Communications in Clinical Pathology and Pharmacology, vol. 29, No. 2, Aug. 1980, pp. 349-360. (Year: 1980).*

(Continued)

*Primary Examiner* — Isaac Shomer
(74) *Attorney, Agent, or Firm* — Saliwanchik, Lloyd & Eisenschenk

(57) ABSTRACT

The present invention relates to a pharmaceutical composition comprising the combination of (i) at least two distinct biocompatible nanoparticles and (ii) at least one compound of interest, typically at least one pharmaceutical compound, to be administered to a subject in need of such at least one compound of interest, wherein the at least two distinct biocompatible nanoparticles potentiate the compound(s) of interest efficiency. The at least two biocompatible nanoparticles can be administered sequentially or simultaneously to the subject but are to be administered separately, typically with an interval of between more than about 5 minutes and about 72 hours, from the at least one compound of interest, preferably before the administration of the at least one compound of interest, to said subject. The longest dimension (Continued)

of the at least two biocompatible nanoparticles is typically between about 4 nm and about 500 nm. The absolute surface charge value of a first biocompatible nanoparticle is of at least |10 mV| and the absolute surface charge value of the second biocompatible nanoparticle, or of any additional biocompatible nanoparticle, has a difference of at least 10 mV with the absolute surface charge value of the first biocompatible nanoparticle.

19 Claims, 3 Drawing Sheets

(52) U.S. Cl.
CPC ........ Y10S 977/773 (2013.01); Y10S 977/906 (2013.01); Y10S 977/907 (2013.01)

(56) References Cited

U.S. PATENT DOCUMENTS

| | | | |
|---|---|---|---|
| 8,845,507 B2 | 9/2014 | Levy et al. | |
| 10,391,058 B2* | 8/2019 | Germain | A61P 35/00 |
| 10,413,509 B2* | 9/2019 | Pottier | A61K 9/5115 |
| 10,765,632 B2* | 9/2020 | Germain | A61K 47/6911 |
| 11,357,724 B2* | 6/2022 | Pottier | A61K 9/0014 |
| 2002/0110586 A1* | 8/2002 | Madden | A61K 9/1272 424/450 |
| 2004/0071768 A1* | 4/2004 | Sarris | A61K 31/475 424/450 |
| 2005/0090732 A1* | 4/2005 | Ivkov | A61N 2/002 600/411 |
| 2006/0264804 A1 | 11/2006 | Karmon et al. | |
| 2007/0036834 A1 | 2/2007 | Pauletti et al. | |
| 2007/0088414 A1* | 4/2007 | Campbell | B82Y 10/00 607/101 |
| 2008/0187595 A1 | 8/2008 | Jordan et al. | |
| 2008/0193372 A1* | 8/2008 | Lanza | A61K 51/1234 424/1.11 |
| 2009/0092661 A1 | 4/2009 | Huang et al. | |
| 2011/0027375 A1 | 2/2011 | Tillement et al. | |
| 2011/0213192 A1 | 9/2011 | Levy et al. | |
| 2012/0157509 A1 | 6/2012 | Hadwiger et al. | |
| 2012/0225128 A1* | 9/2012 | Jordan | A61K 9/5146 424/497 |
| 2014/0056813 A1 | 2/2014 | Pottier et al. | |
| 2014/0186447 A1 | 7/2014 | Desai | |
| 2014/0271489 A1 | 9/2014 | Grinstaff et al. | |
| 2016/0184225 A1 | 6/2016 | Pottier et al. | |
| 2016/0310614 A1 | 10/2016 | Pottier et al. | |
| 2017/0258718 A1 | 9/2017 | Meyre et al. | |
| 2017/0258720 A1 | 9/2017 | Pottier et al. | |
| 2017/0258721 A1 | 9/2017 | Germain et al. | |
| 2017/0258937 A1 | 9/2017 | Meyre et al. | |

FOREIGN PATENT DOCUMENTS

| | | |
|---|---|---|
| EP | 2 537 530 | 12/2012 |
| FR | 2 922 106 | 4/2009 |
| JP | H10-120597 | 5/1998 |
| WO | WO 96/35415 | 11/1996 |
| WO | WO 99/08676 | 2/1999 |
| WO | WO 2005/063305 | 7/2005 |
| WO | WO 2005/086639 | 9/2005 |
| WO | WO 2007/116954 | 10/2007 |
| WO | WO 2007/128066 | 11/2007 |
| WO | WO 2009/081287 | 7/2009 |
| WO | WO 2009/105774 | 8/2009 |
| WO | WO 2009/142754 | 11/2009 |
| WO | WO 2009/147214 | 12/2009 |
| WO | WO 2010/048623 | 4/2010 |
| WO | WO 2011/070324 | 6/2011 |
| WO | WO 2011/119988 | 9/2011 |
| WO | WO 2011/151631 | 12/2011 |
| WO | WO 2012/051220 | 4/2012 |
| WO | WO 2012/104275 | 8/2012 |
| WO | WO 2012/104277 | 8/2012 |
| WO | WO 2014/039874 | 3/2014 |
| WO | WO 2014/057432 | 4/2014 |
| WO | WO 2014/191569 | 12/2014 |
| WO | WO 2015/091888 | 6/2015 |

OTHER PUBLICATIONS

He, C. et al. "Effects of particle size and surface charge on cellular uptake and biodistribution of polymeric nanoparticles" *Biomaterials*, May 1, 2010, pp. 3657-3666, vol. 31, No. 13.
"NCL Method PCC-2 Measuring Zeta Potential of Nanoparticles" Nov. 1, 2009, Retrieved from the Internet: URL:http://ncl.cancer.gov/NCL_Method_PCC-2.pdf on Feb. 23, 2015, pp. 1-14.
Written Opinion in International Application No. PCT/EP2015/077446, dated Feb. 3, 2016, pp. 1-6.
Belisario, M. A. et al. "Effect of avarol, avarone and nine of their natural and synthetic derivatives on microsomal drug-metabolizing enzymes" *Toxicology Letters*, 1991, pp. 183-193, vol. 57.
Michalets, E. L. et al. "Update: Clinically Significant Cytochrome P-450 Drug Interactions" *Pharmacotherapy*, 1998, pp. 84-112, vol. 18, No. 1.
Written Opinion in International Application No. PCT/EP2015/077441, dated Feb. 3, 2016, pp. 1-6.
Babcock, J. J. et al. "Bovine serum albumin oligomers in the E- and B-forms at low protein concentration and ionic strength" *International Journal of Biological Macromolecules*, Feb. 1, 2013, pp. 42-53, vol. 53.
Ma, P. et al. "Paclitaxel Nano-Delivery Systems: A Comprehensive Review" *Journal of Nanomedicine and Nanotechnology*, Jan. 1, 2013, pp. 1-16, vol. 4, No. 2.
Written Opinion in International Application No. PCT/EP2015/077423, dated Jan. 21, 2016, pp. 1-5.
Banquy, X. et al. "Effect of mechanical properties of hydrogel nanoparticles on macrophage cell uptake" *Soft Matter*, Jan. 1, 2009, pp. 3984-3991, vol. 5, No. 20.
Written Opinion in International Application No. PCT/EP2015/077438, dated Jan. 27, 2016, pp. 1-7.
Written Opinion in International Application No. PCT/EP2015/077425, dated Jan. 15, 2016, pp. 1-6.
DeKrafft, K.E. et al. "Zr-and Hf-based nanoscale metal-organic frameworks as contrast agents for computed tomography" *Journal of Materials Chemistry*, Sep. 21, 2012, pp. 18139-18144, vol. 22, No. 35.
Maggiorella, L. et al. "Nanoscale radiotherapy with hafnium oxide nanoparticles" *Future Oncology*, Sep. 1, 2012, pp. 1167-1181, vol. 8, No. 9.
Written Opinion in International Application No. PCT/EP2014/078619, dated Mar. 26, 2015, pp. 1-6.
Abu Lila, A. S. et al. "Oxaliplatin encapsulated in PEG-coated cationic liposomes induces significant tumor growth suppression via a dual-targeting approach in a murine solid tumor model" *Journal of Controlled Release*, 2009, pp. 8-14, vol. 137.
Gabizon, A. A. "Liposome circulation time and tumor targeting: implications for cancer chemotherapy" *Advanced Drug Delivery Reviews*, 1995, pp. 285-294, vol. 16.
Ogu, C. C. et al. "Drug interactions due to cytochrome P450" *BUMC Proceedings*, Oct. 2000, pp. 421-423, vol. 13.
Harashima, H. et al. "Size Dependent Liposome Degradation in Blood: In Vivo/In Vitro Correlation by Kinetic Modeling" *Journal of Drug Targeting*, 1995, pp. 253-261, vol. 3.
Hadaruga, D. I. et al. "Liposomes containing titanium dioxide nanoparticles (Short communication)" *Journal of Agroalimentary Processes and Technologies*, 2010, pp. 62-66, vol. 16, No. 1.
Shamsipour, F. et al. "Conjugation of Monoclonal Antibodies to Super Paramagnetic Iron Oxide Nanoparticles for Detection of her2/neu Antigen on Breast Cancer Cell Lines" *Journal of Medical Biotechnology*, Ap.-Jun. 2009, pp. 27-31, vol. 1, No. 1.
Kim, J-Y. et al. "In-vivo tumor targeting of pluronic-based nano-carriers" *Journal of Controlled Release*, 2010, pp. 109-117, vol. 147.

(56) References Cited

OTHER PUBLICATIONS

Yu, M. K. et al. "Drug-Loaded Superparamagnetic Iron Oxide Nanoparticles for Combined Cancer Imaging and Therapy In Vivo" *Angew. Chem. Int. Ed.*, 2008, pp. 5362-5365, vol. 47.
Choi, W. I. et al. "The effect of mechanical properties of iron oxide nanoparticle-loaded functional nano-carrier on tumor targeting and imaging" *Journal of Controlled Release*, 2012, pp. 267-275, vol. 162.
Liang, X. et al. "Mechanical properties and stability measurement of cholesterol-containing liposome on mica by atomic force microscopy" Journal of Colloid and Interface Science, 2004, pp. 53-62, vol. 278.
Nie, Y. et al. "Cholesterol Derivatives Based Charged Liposomes for Doxorubicin Delivery: Preparation, In Vitro and In Vivo Characterization" *Theranostics*, 2012, pp. 1092-1103, vol. 2, No. 11.
Bhatt, N. et al. "Stability study of O/W emulsions using zeta potential" *Journal of Chemical and Pharmaceutical Research*, 2010, pp. 512-527, vol. 2, No. 1.
Yu, S. et al. "Carboxyl group (–$CO_2H$) functionalized ferrimagnetic iron oxide nanoparticles for potential bio-applications" *Journal of Materials Chemistry*, 2004, pp. 2781-2786, vol. 14.
Ismail, M.F. et al. "Potential therapeutic effect of nanobased formulation of rivastigmine on rat model of Alzheimer's disease" *International Journal of Nanomedicine*, 2013, pp. 393-406, vol. 8.
Bowen, P., "Particle Size Distribution Measurement from Millimeters to Nanometers and from Rods to Platelets," *Journal of Dispersion Science and Technology*, Jan. 1, 2002, vol. 23, No. 5, pp. 631-662.
Written Opinion in International Application No. PCT/EP2014/061296, dated Sep. 5, 2014, pp. 1-9.
Thongborisute, J. et al. "Properties of Liposomes coated with hydrophobically modified chitosan in oral liposomal drug delivery" *Pharmazie*, 2006, pp. 106-111, vol. 61.
Olson, F. et al. "Preparation of Liposomes of Defined Size Distribution by Extrusion Through Polycarbonate Membranes" *Biochimica et Biophysica Acta*, 1979, pp. 9-23, vol. 557.
Lu, H. et al. "Drug-target residence time: critical information for lead optimization" *Current Opinion in Chemical Biology*, 2010, pp. 467-474, vol. 14.
Copeland, R. A. et al. "Drug-target residence time and its implications for lead optimization" *Nature Reviews/Drug Discovery*, Sep. 2006, pp. 730-739, Corrigendum (1 page), vol. 5.
Simoes, S. et al. "Cationic liposomes for gene delivery" *Expert Opinion in Drug Delivery*, 2005, pp. 237-254, vol. 2, No. 2.
Singh, R. et al. "Nanoparticle-based targeted drug delivery" *Experimental and Molecular Pathology*, 2009, pp. 215-223, vol. 86.
Lai, B.-H. et al. "Surface modification of iron oxide nanoparticles with polyarginine as a highly positively charged magnetic nano-adsorbent for fast and effective recovery of acid proteins" *Process Biochemistry*, 2012, pp. 799-805, vol. 47.
Abra, RM. et al. "Liposome Disposition in Vivo: Effects of Pre-Dosing with Liposomes" *Research Communications in Chemical Pathology and Pharmacology*, Aug. 1980, pp. 349-360, vol. 29, No. 2.
Colbern, G. T. et al. "Significant Increase in Antitumor Potency of Doxorubicin HCl by Its Encapsulation in Pegylated Liposomes" *Journal of Liposome Research*, 1999, pp. 523-538, vol. 9, No. 4.
Yong, S.-B. et al. "Mononuclear phagocytes as a target, not a barrier, for drug delivery" *Journal of Controlled Release*, 2017, pp. 53-61, vol. 259.
Kiani, J. et al. "Medicinal importance of grapefruit juice and its interaction with various drugs" *Nutrition Journal*, 2007, pp. 1-9, vol. 6, No. 33.
Ohta, T. et al. "Paradisin C: a new CYP3A4 inhibitor from grapefruit juice" *Tetrahedron*, 2002, pp. 6631-6635, vol. 58.
UChicago News "Grapefruit juice boosts drug's anti-cancer effects" Obtained from internet on Oct. 23, 2018, originally published on Apr. 20, 2009, https://news.uchicago.edu/story/grapefruit-juice-boosts-drugs-anti-cancer-effects, pp. 1-4.
Uesawa, Y. et al. "Relationship between Lipophilicities of 1,4-Dihydropyridine Derivatives and Pharmacokinetic Interaction Strengths with Grapefruit Juice" *The Pharmaceutical Society of Japan*, 2008, pp. 117-122, vol. 128, No. 1.

\* cited by examiner

PHARMACEUTICAL COMPOSITION COMBINING AT LEAST TWO DISTINCT NANOPARTICLES AND A PHARMACEUTICAL COMPOUND, PREPARATION AND USES THEREOF

CROSS-REFERENCE TO RELATED APPLICATIONS

This application is a continuation of U.S. application Ser. No. 15/529,101, filed May 24, 2017, now U.S. Pat. No. 10,391,058, which is the U.S. national stage application of International Patent Application No. PCT/EP2015/077446, filed Nov. 24, 2015.

FIELD OF THE INVENTION

The invention relates to a pharmaceutical composition comprising the combination of (i) at least two distinct biocompatible nanoparticles and (ii) at least one compound of interest, typically at least one pharmaceutical compound, to be administered to a subject in need of such at least one compound of interest, wherein the at least two distinct biocompatible nanoparticles potentiate the compound(s) of interest efficiency.

The at least two biocompatible nanoparticles can be administered sequentially or simultaneously to the subject but are to be administered separately, typically with an interval of between more than about 5 minutes and about 72 hours, from the at least one compound of interest, preferably before the administration of the at least one compound of interest, to said subject.

The longest dimension of the at least two biocompatible nanoparticles is typically between about 4 nm and about 500 nm. The absolute surface charge value of a first biocompatible nanoparticle is of at least 10 mV (|10 mV|) and the absolute surface charge value of the second biocompatible nanoparticle, or of any additional biocompatible nanoparticle, has a difference of at least 10 mV with the absolute surface charge value of the first biocompatible nanoparticle.

The combined, typically sequential, administration to the subject of the at least two distinct biocompatible nanoparticles together with the at least one compound of interest maintains the pharmaceutical (i.e. therapeutic, prophylactic or diagnostic) benefit of said at least one compound of interest for a reduced toxicity thereof in said subject, or increases its pharmaceutical benefit for an equivalent or reduced toxicity, when compared to the pharmaceutical benefit and toxicity induced by said at least one compound when administered at the standard pharmaceutical dose(s).

The pharmaceutical composition of the invention typically allows a reduction of at least 10% of the administered compound pharmaceutical dose when compared to the standard pharmaceutical dose of the at least one compound of interest while maintaining the same pharmaceutical benefit for an equivalent toxicity, preferably a reduced toxicity, for the subject, or while increasing the pharmaceutical benefit for an equivalent or reduced toxicity for the subject.

BACKGROUND

In order to ensure safety and efficacy, therapeutic compounds are required to be selectively delivered to their target site at an optimal rate in the subject in need thereof.

Pharmacokinetics (pK) is a branch of pharmacology dedicated to the determination of the fate of substances administered externally to a living organism. This determination involves steps of measuring compound's concentrations in all major tissues over a long enough period of time, preferably until the compound's elimination. Pharmacokinetics is necessary to efficiently describe the compound's behavior in vivo, including the mechanisms of its absorption and distribution as well as its chemical changes in the organism. The pK profile in the blood can be fitted using various programs to obtain key pK parameters that quantitatively describe how the body handles the compound. Important parameters include maximum concentration ($C_{max}$), half-life ($t_{1/2}$), clearance, area under curve (AUC), and mean resident time (MRT), i.e. the average time during which a compound stays in an organism. When a prolonged blood circulation of the compound formulation is observed, it is usually associated to an increased $t_{1/2}$, a reduced clearance, an increased AUC, and an increased MRT. pK data are often used in deciding the optimal dose and dose regimen for maintaining the desirable blood concentration in order to improve therapeutics' efficiency with minimal side effects. In addition, as well known by the skilled person, the blood concentration of a compound is correlated with both its efficacy and toxicity in most cases, typically for free drugs.

The physico-chemical properties of therapeutic as well as prophylactic compounds have an important impact on their pharmacokinetic and metabolic fate in the body. Therefore, selection of appropriate physico-chemical properties is key when designing such a compound. However, since the compound is not always endogenously provided by the organism itself and is usually externally administered, its biodistribution profile has to be optimized in order to fit with, and preferably optimize, the desired pharmacological action thereof.

Several approaches have been explored to optimize the delivery of a compound to its target site. A strategy is to design a therapeutic compound with stealth properties to prolong its blood half-life and consequently, to enhance its accumulation to the target site. One favorable approach is the covalent attachment of polyethylene glycol (PEG) to the therapeutic compound that has proved to increase the in vivo half-life ($t_{1/2}$) of the circulating compound, the level of the in vivo half-life increase varying depending partly on the nature of the compound and on that of the coating. Also, drug carriers such as liposomes, emulsions or micelles have been developed to enhance therapeutic efficacy of drugs by modifying their biodistribution profile in the subject's body.

However, lack of selectivity in the biodistribution of the therapeutic compounds still remains a concern. So far, poor pharmacokinetics and high toxicity are important causes of failure in therapeutic compounds development.

As an example, in the context of cancer treatment, intentional inhibition of essential functions of the body in order to kill cancer cells results in toxicity in normal cells, and clinicians have to rely on differences in dose-response and therapeutic compounds distribution between tumors and normal tissues to find a possible therapeutic window. Of note, hepatotoxicity remains a major reason for drug withdrawal from pharmaceutical development and clinical use due to direct and indirect mechanisms of drug-induced cell injury in the liver.

An approach proposed for nanoparticulate compounds such as drug carriers [*Critical Reviews in Therapeutic Drug Carrier Systems* 110:31-59 1994] is to pre-inject a decoy carrier to decrease, saturate, or even inactivate the phagocytic capacity of the reticuloendothelial system (RES). Impairment or blockade may also be associated with decreased plasma levels of opsonic molecules. Intravenous administration of certain agents, such as alkyl esters of fatty acids, dextran sulfate, salts of rare earth elements (e.g. GdCl$_3$), drug carriers, either empty or encapsulating clodronate, prior to administration of test particles, has been demonstrated to induce moderate to dramatic reduction in kupffer cells uptake.

For instance, authors in "*Biomimetic amplification of nanoparticle homing to tumors*" [*PNAS* 2007], reported the role of RES in the clearance of their nanoparticles "CREKA-SPIO". Initial experiments showed that intravenous (IV) injected "CREKA-SPIO" nanoparticles did not effectively accumulate in MDA-MB-435 breast cancer xenografts. In contrast, a high concentration of particles was seen in RES tissues. By depleting RES macrophages in the liver with liposomal clodronate, they found a 5-fold prolongation of their particle's half-life. However, clodronate agent induces the apoptosis of macrophages from liver and spleen, and this is considered as globally detrimental as macrophages depletion increases the risks associated to immunosuppression and infection. In a second experiment, the authors tested liposomes coated with chelated Ni (II) as a potential decoy particle hypothesizing that iron oxide and Ni (II) would attract similar plasma opsonins, and that Ni-liposomes could therefore deplete them in the systemic circulation. Indeed, intravenous (IV) injected Ni-liposomes, whether administered 5 minutes or 48 hours before the injection of CREKA-SPIO nanoparticles, allows a five-fold increase of the nanoparticles' blood half-life. However, high toxicity was observed causing deaths among tumor mice. Plain liposomes were also tested instead of Ni-liposomes. However, while reducing the toxicity when compared to said Ni-liposomes, plain liposomes were far less effective than them. Indeed, the blood half-life increase was only of a factor about 2.

WO2005086639 relates to methods of administering a desired agent selectively to a target site in a subject, typically in the context of ultrasound or X-ray exposure, or in the context of magnetic resonance imaging (MM), as well as in the context of therapy. The aim of the described method is to improve or maintain the efficiency of the agent of interest while reducing the total dose of agents concretely administered thanks to concomitant administration of a decoy inactive carrier.

The described invention employs a probability-based approach. A non-targeted inactive agent ("inactive carrier") is co-administered (i.e. "substantially simultaneously") with a targeted agent of interest (present in an "active composition") exhibiting similar physical features, in order to facilitate the evasion of the RES system by the targeted agent of interest thereby allowing an improved uptake of the agent of interest at the desired site. This approach results in a lower exposure of patients to the agent of interest and, as a consequence, in a lower per dosage cost of said agent of interest. The active composition and the decoy inactive carrier are administered within five minutes of each other, preferably within 2 minutes of each other, or even less. This approach relies on the presence of a large excess of untargeted "carrier" or "decoy" vehicles and on the probability that this decoy carrier in excess will compete with the targeted agent of interest for an uptake by the reticuloendothelial system when supplied in the presence of vehicles that are targeted to a desired location. The half-life of particles captured by RES is dose dependent, i.e. the circulating half-life of particles increases as the dosage increases. The slower clearance associated to higher dosages is thought to favor the maintaining of a total agents high concentration allowing a decrease of the dose of the agent of interest which is to be administered. In other words, an increased half-life of total agents due to a global higher dosage thereof should be beneficial to the targeted agents, according to the authors of WO2005086639. The requirement involved by this approach is that the active agent and the inactive one behave similarly with regard to their clearance characteristics in the RES, whatever their respective compositions.

In this approach, the quasi-concomitant injection of the inactive agent and of the active one is required to increase the global amount of agents present in the blood and consequently to prolong their blood half-life. Such strategy, which expressly relies on a probability-based approach, necessarily requires the association of the active agent with a targeting agent in order to achieve its successful accumulation on the target site by conferring said active agent an advantage over the inactive one. In addition, due to the quasi-concomitant injection, a specific design of the inactive carrier may be required depending on the intended use of the active composition.

WO2005/063305 relates to an assembly comprising a gas-filled microvesicle (with a size typically of at least 0.5 µm) and a component (with a size about below 100 nm) associated to said microvesicle. The resulting assembly is to be used as a pharmaceutically active component in diagnostically and/or therapeutically active formulations. The two components, i.e. the gas-filled microvesicle and the microvesicle associated component, are administered simultaneously typically for enhancing the imaging in the field of ultrasound contrast imaging, including targeted ultrasound imaging, ultrasound-mediated drug delivery and other imaging techniques.

As apparent from the prior art and despite of a long medical need, the improvement of compounds (including therapeutic, prophylactic as well as diagnostic compounds) which cannot be efficiently used in patients due to their unacceptable toxicity or to their unfavorable pharmacokinetics parameters remains a concern.

DETAILED DESCRIPTION

The present invention now allows optimization of the efficiency of a compound of interest (herein also simply identified as "the compound"), or of a combination of compounds of interest, whatever its (their) intended use in the context of therapy, prophylaxis or diagnostic. The composition herein described which is a combination of (i) at least two distinct biocompatible nanoparticles and of (ii) at least one compound of interest, typically at least one pharmaceutical compound (i.e. a therapeutic, prophylactic or diagnostic compound), optimize the at least one compound of interest pharmacokinetic parameters, and, as a consequence, now renders possible the development of therapeutic compounds which could not have been developed otherwise due for example to their unacceptable toxicity. Typically, the biocompatible nanoparticle is not used as such as a pharmaceutical compound, i.e. as a therapeutic, prophylactic or diagnostic compound.

A typical composition of the invention (herein generally identified as "pharmaceutical composition") is a composition comprising the combination of (i) at least two distinct biocompatible nanoparticles and (ii) at least one compound ("the compound of interest"), wherein the longest or largest dimension of each of the at least two biocompatible nanoparticles is typically between about 4 nm and about 500 nm, the absolute surface charge value of a first biocompatible nanoparticle (also herein identified as the "first" biocompatible nanoparticle) is of at least 10 mV (|10 mV|) and the absolute surface charge value of a second biocompatible nanoparticle (also herein identified as the "second" biocompatible nanoparticle), or of any additional biocompatible nanoparticle, has a difference of at least 10 mV with the absolute surface charge value of the first biocompatible nanoparticle.

Typically, the ratio between the (at least two distinct) biocompatible nanoparticles and compounds of interest is between 0.1/1 and 1000/1 or 0.5/1 and 1000/1, preferably between 0.5/1 and 500/1, even more preferably between 0.5/1 and 300/1.

The terms "about" and "around" when associated to a value such as for example a nanoparticle's size or a time interval indicates that a variation with the indicated value, which would be recognized by the skilled person as small variation, does not substantially impact the properties of the subject-matter it is associated to and that said subject-matter remains in the spirit of the claimed invention.

A preferred object of a the invention is a pharmaceutical composition comprising the combination of (i) at least two distinct biocompatible nanoparticles and of (ii) at least one pharmaceutical compound, wherein the longest or largest dimension of each of the at least two biocompatible nanoparticles is between about 4 nm and about 500 nm, the absolute surface charge value of a first biocompatible nanoparticle is of at least 10 mV (|10 mV|) and the absolute surface charge value of a second biocompatible nanoparticle, or of any additional biocompatible nanoparticle, has a difference of at least 10 mV with the absolute surface charge value of the first biocompatible nanoparticle, said composition being for use for administering the at least two distinct biocompatible nanoparticles in a subject in need of the at least one pharmaceutical compound separately from the administration of said at least one pharmaceutical compound to said subject, typically with an interval of between more than 5 minutes and about 72 hours, and wherein the biocompatible nanoparticle is not used as such as a pharmaceutical compound.

The combined administration to the subject of the at least two distinct biocompatible nanoparticles and of the at least one compound of interest, through the composition of the invention, typically allows (maintains) the same pharmaceutical (i.e. therapeutic, prophylactic or diagnostic) benefit of the at least one compound for a reduced toxicity thereof for the subject, or increase the pharmaceutical benefit of the at least one compound for an equivalent or reduced toxicity thereof for the subject (preferably a reduced toxicity), when compared to pharmaceutical benefit and toxicity induced by the standard pharmaceutical dose(s) of said at least one compound.

The pharmaceutical composition of the invention typically allows a reduction of at least 10%, preferably at least 15%, of the administered at least one pharmaceutical (i.e. therapeutic, prophylactic or diagnostic) compound dose when compared to the standard pharmaceutical dose of said compound (i) while maintaining the same pharmaceutical benefit for an equivalent toxicity, preferably a reduced toxicity, for the subject or (ii) while increasing the pharmaceutical benefit for an equivalent or reduced toxicity for the subject.

As the shape of the particle can influence its "biocompatibility", particles having a quite homogeneous shape are herein preferred. For pharmacokinetic reasons, nanoparticles being essentially spherical/round or ovoid in shape are thus preferred. Such a shape also favors the nanoparticle interaction with or uptake by cells. Spherical/round shape is particularly preferred.

In the spirit of the invention, the term "nanoparticle" refers to a product, in particular a synthetic product, with a size in the nanometer range, typically between about 1 nm and about 500 nm, preferably between about 4 nm and about 500 nm, between about 4 and about 400 nm, about 30 nm and about 300 nm, about 20 nm and about 300 nm, about 10 nm and about 300 nm, for example between about 4 nm and about 100 nm, for example between about 10 nm, 15 nm or 20 nm and about 100 nm, or between about 100 nm and about 500 nm, typically between about 100 nm and about 300 nm.

The terms "size of the nanoparticle", "largest size of the nanoparticle" and "longest size of the nanoparticle" herein typically refer to the "longest or largest dimension of the nanoparticle" or "diameter of the nanoparticle" when spherical/round or ovoid in shape. Transmission Electron Microscopy (TEM) or Cryo-TEM can be used to measure the size of the nanoparticle. As well, Dynamic Light Scattering (DLS) can be used to measure the hydrodynamic diameter of nanoparticles in solution. These two methods may further be used one after each other to compare the hydrodynamic diameter of a nanoparticle measured by DLS with the size of said nanoparticle measured by TEM or Cryo-TEM, in order to confirm said size. A preferred method is DLS (Ref. International Standard ISO22412 Particle Size Analysis—Dynamic Light Scattering, International Organisation for Standardisation (ISO) 2008).

To be usable in the context of the invention, the absolute electrostatic surface charge (also herein identified as "charge" or "surface charge") of the "first" biocompatible nanoparticle is to be of at least, preferably higher than, |10 mV| (absolute value) and the surface charge value of the "second" biocompatible nanoparticle, or of any additional biocompatible nanoparticle, has to have a difference of at least 10 mV with the absolute surface charge value of the "first" biocompatible nanoparticle. The surface charge of a nanoparticle is typically determined by zeta potential measurements in aqueous medium for a nanoparticles concentration between 0.2 and 10 g/L, for a pH between 6 and 8, and typically for electrolytes concentrations in the aqueous medium between 0.001 and 0.2 M, for example 0.01 M or 0.15 M.

Typically, the "first" biocompatible nanoparticle of the present invention has an electrostatic surface charge of at least |10 mV|, i.e. below −10 mV or above +10 mV, for example below between −12 mV or −15 mV and −20 mV or above between +12 mV or +15 mV and +20 mV, typically below −15 mV or above +15 mV. The "second" biocompatible nanoparticle, or of any additional biocompatible nanoparticle, has a (positive or negative) difference of at least 10 mV with the absolute surface charge value of the first biocompatible nanoparticle.

Preferably, the "first" biocompatible nanoparticle of the present invention has an absolute electronic surface charge value ("absolute surface charge value") of more than 10 mV, said charge being even more preferably a negative charge.

The combined properties, size and surface charge of the at least two distinct biocompatible nanoparticles, allow for a short blood circulation of the least two distinct nanoparticles. Therefore, by sequentially administering at least two distinct biocompatible nanoparticles of the invention and the compound(s) of interest, no co-circulation or a limited co-circulation of the at least two distinct biocompatible nanoparticles and of the compound of interest is achieved. Therefore, the combined properties of the at least two distinct biocompatible nanoparticles, size and surface charge, permit the safe use of the compound(s) of interest while allowing (maintaining) the same pharmaceutical (i.e. therapeutic, prophylactic or diagnostic) benefit of the at least one compound for a reduced toxicity thereof for the subject, or in other words while increasing the pharmaceutical benefit of the at least one compound for an equivalent or reduced toxicity thereof for the subject (preferably a reduced toxicity), when compared to pharmaceutical benefit and toxicity induced by the standard pharmaceutical dose(s) of said at least one compound.

The at least two biocompatible nanoparticles usable in the context of the invention can all be either organic or inorganic. A mixture of organic and inorganic nanoparticles can further be used as the at least two biocompatible particles.

When organic, the nanoparticles present in the pharmaceutical composition of the invention can be lipid-based nanoparticles (glycerolipid, phospholipid, sterol lipid, etc.), such as solid-lipid nanoparticles, protein-based nanoparticles also herein identified as "protein-nanoparticles" (albumin for instance), polymer-based nanoparticles ("polymeric nanoparticles"), co-polymer-based nanoparticles ("co-polymeric nanoparticles"), carbon-based nanoparticles, virus-like nanoparticles (for example viral vectors) or a mixture thereof.

The organic nanoparticles may further be nanospheres (plain nanoparticles) or nanocapsules (hollow nanoparticles) such as liposomes, gels, hydrogels, micelles, dendrimers, etc. A mixture of the herein described organic nanoparticles can also be used.

The polymer or co-polymer can be of natural or synthetic origin.

Examples of synthetic (artificial) and natural polymers or co-polymers usable in the context of the invention to prepare organic nanoparticles can be selected from polylactic acid (PLA), Poly (lactide-co-glycolic) acid (PLGA), Polyethyleneglycol (PEG), Polyglactin, Polylactide, Polyoxyethylene fatty acid esters, Polypropylene glycol, Polysorbate, Polyvinyl alcohol, Polyacrylamide, Polymethylmethacrylate, Polyalkylcyanoacrylate, Polylactate-co-glycolate, Poly (amido amine), Poly(ethyleneimine), alginate, cellulose and cellulose derivatives polymers, collagen, hyaluronic acid, polyglutamic acid (PGA), actin, polysaccharide, and gelatin.

When inorganic and when its longest dimension is typically below about 10 nm, for example below about 8 nm, below about 7 nm, typically comprised between about 7 nm and about 4 nm, for example below about 6 nm, below about 5 nm or below about 4 nm, the nanoparticle may be made of any inorganic material. The inorganic material may for example comprise metallic element from period 3, 4, 5, 6 of the Mendeleev's periodic table, including the lanthanides. When the longest dimension of the nanoparticle is typically below about 10 nm, the nanoparticles may assemble in larger structures. Assembling of nanoparticles in larger structure may typically be triggered by interactions between nanoparticles and a biocompatible polymer(s), protein(s), etc. Larger structure may also be obtained by trapping the nanoparticles in a carrier, typically a plain carrier such as gelatin structure (also herein identified as "gelatin nanoparticle") or a hollow carrier such as liposome. After in vivo administration, those larger structures may further release the nanoparticle(s).

When inorganic and when the longest dimension of said nanoparticle is typically of at least 10 nm, typically between 10 and 500 nm, the nanoparticle may comprise at least one of, or may consist in (i) one or more divalent metallic elements selected for example from Mg, Ca, Ba and Sr, (ii) one or more trivalent metallic element selected for example from Fe and Al, and (iii) one or more tetravalent metallic element comprising Si.

In a particular embodiment, the inorganic material of the nanoparticle is selected from (i) one or more divalent metallic elements selected for example from Mg, Ca, Ba and Sr (ii) one or more trivalent metallic element selected for example from Fe and Al and (iii) one or more tetravalent metallic element comprising Si.

In a further particular embodiment, the inorganic material of the nanoparticle is selected from calcium carbonate ($CaCO_3$), magnesium carbonate ($MgCO_3$), magnesium hydroxide ($Mg(OH)_2$), iron hydroxide ($Fe(OH)_2$), iron oxyhydroxide (FeOOH), iron oxide ($Fe_3O_4$ or $Fe_2O_3$), aluminium oxide ($Al_3O_4$), aluminium hydroxide ($Al(OH)_3$), aluminium oxyhydroxide (AlOOH) and silicium oxide ($SiO_2$).

The nanoparticles used in the herein described compositions are to be biocompatible, i.e. compatible with living tissues. When required by their composition, the nanoparticles are thus to be coated with a biocompatible material to become usable. In a particular embodiment of the invention, the herein mentioned nanoparticle is thus covered with a biocompatible coating.

The biocompatible material can be an agent allowing interaction with a biological target.

An agent forming a positive charge on the nanoparticle's surface can be for example selected from aminopropyltriethoxisilane or polylysine. An agent forming a negative charge on the nanoparticle surface can be for example selected from a phosphate (for example a polyphosphate, a metaphosphate, a pyrophosphate, etc.), a carboxylate (for example citrate or dicarboxylic acid, in particular succinic acid) or a sulphate.

In a particular embodiment, as long as the absolute charge of the "first" nanoparticle is of at least 10 mV (|10 mV|) and the absolute surface charge value of a second biocompatible nanoparticle, or of any additional biocompatible nanoparticle, has a difference of at least 10 mV with the absolute surface charge value of the first biocompatible nanoparticle, the at least two distinct nanoparticles can be coated with a biocompatible material selected from an agent displaying a steric group. Such a group may be selected for example from polyethylene glycol (PEG); polyethylenoxide; polyvinylalcohol; polyacrylate; polyacrylamide (poly(N-isopropylacrylamide)); polycarbamide; a biopolymer; a polysaccharide such as dextran, xylan and cellulose; collagen; a switterionic compound such as polysulfobetain; etc.

The biocompatible coating may further comprise a labelling agent, typically an agent allowing the visualisation of a color using standard imaging equipment.

The combined administration of the at least two distinct biocompatible nanoparticles together with the at least one compound of interest maintains the pharmaceutical benefit (i.e. therapeutic, prophylactic or diagnostic benefit), typically the therapeutic benefit, of the compound of interest for a reduced toxicity, or increases the pharmaceutical benefit of the compound for an equivalent or reduced toxicity, for the subject, typically when said at least two nanoparticles are (simultaneously or separately) administered to the subject in need of the at least one compound of interest separately from said at least one compound of interest, preferably with an interval of between more than 5 minutes and about 72 hours when compared to pharmaceutical benefit and toxicity induced by the standard pharmaceutical, typically therapeutic, dose(s) of said at least one compound of interest in the absence of any particles.

In a particular embodiment, the combined administration of the at least two distinct biocompatible nanoparticles and of the at least one compound of interest allows a reduction of at least 10%, preferably at least 15%, of the administered compound therapeutic dose, typically when administered in the subject in need of the at least one compound of interest separately from said at least one compound of interest, typically with an interval of between more than 5 minutes and about 72 hours before or after, preferably before, said compound of interest, when compared to the standard therapeutic dose of said compound while maintaining the same therapeutic benefit for an equivalent toxicity or a reduced toxicity (preferably a reduced toxicity) of the compound(s) for the subject; or while increasing the therapeutic benefit for an equivalent or reduced toxicity of the compound(s) for the subject.

In a particular embodiment, nanoparticles are administered with several compounds of interest, typically two compounds of interest.

The nanoparticles are preferably cleared from the subject to whom it has been administered typically within 1 hour and 6 weeks, for example 4 weeks, within 1 hour and 1 month, for example between 1 hour and 3 weeks, or between 1 hour and 2 weeks, or between 1 hour and 1 week, following their administration to a subject in need of the compound of interest.

The material constituting a nanoparticle (including its biocompatible coating when present) is important in determining the biopersistence of the nanoparticle. The nanoparticle may be regarded as biodegradable (when constituted for example by a biodegradable polymer such as PLGA or PLA), dissolvable (iron oxide for example) or non-biodegradable and non-dissolvable. Biodegradable and dissolvable nanoparticles facilitate rapid nanoparticle clearance from the subject.

Different molecules or agents can be used according to the present teaching as the at least one compound of interest, typically as the at least one pharmaceutical compound of interest, administered in combination with the at least two distinct biocompatible nanoparticles as described hereinabove. This compound may be a therapeutic, a prophylactic or a diagnostic compound as previously explained. It can be an organic compound or an inorganic compound.

Examples of organic compound usable as the compound of interest can be selected from a biological compound, an antibody, an oligonucleotide, a synthesized peptide, a small molecule targeted therapeutic, an oncolytic virus, a cytotoxic compound, and any corresponding prodrug or derivative thereof, etc.

In a particular embodiment, the compound of interest used in the context of the present invention is an organic compound preferably selected from a biological compound, a small molecule targeted therapeutic, an oncolytic virus, and a cytotoxic compound. In another particular embodiment, the compound of interest is selected from an antibody, an oligonucleotide, and a synthesized peptide.

A biological compound is for instance an antibody, an antibody drug conjugate, preferably a monoclonal antibody ("mAb"), such as infliximab, adalimumab, bevacizumab, rituximab, trastuzumab, ranibizumab, cetuximab, panatimumab; a protein or a recombinant protein such as enbrel (etanercept) or interferon beta-1a; a peptide or a recombinant peptide such as insulin glargine or betaseron; a vaccine such as prevnar 13 or gardasil; a biosimilar such as epogin; an enzyme or a recombinant enzyme such as replagal or creon; etc.

An oligonucleotide is for instance an antisense oligonucleotide, an aptamer, such as mipomersen sodium or pursennid, etc.

A synthesized or artificial peptide is for instance glatiramer acetate or leuprolide acetate.

An oncolytic virus is a therapeutically useful virus that selectively infects and damages cancerous tissues without causing harm to normal tissues. Oncolytic virus is for instance selected from an adenovirus such as Onyx-015, a coxsackie virus such as Catavak, a herpes simplex virus such as talimogene laherparepvec, a maesla virus such as MV-CEA, a newcastle disease virus, a parvovirus, a poliovirus, a reovirus, a Seneca valley virus, a retrovirus, a vaccinia, a vesicular stomatitis virus.

A small molecule targeted therapeutic generally inhibits enzymatic domains on mutated, overexpressed, or otherwise critical protein (potential target in the context of cancer treatment) within the malignant cells. Some therapeutics agents include those that target cell division (for example an aurora-kinase inhibitor or a cyclin-dependent-kinase inhibitor), as well as other biological mechanisms such as protein turnover and chromatin modification (for example a histone-deacetylase inhibitor). Small molecules targeted therapeutics are for instance imatinib, rapamycin, gefitinib, erlotinib, sorafenib, sunitinib, nilotinib, dasatinib, lapatinib, bortezomib, atorvastatin, etc.

A cytotoxic compound is for instance a DNA-modifying agent, such as an anthracycline (for example doxorubicine, daunorubicine, etc.), an alkylating agent (for example melphalan or temozolomide), as well as a drug interfering very precisely with defined physiological mechanisms such as microtubule polymerization (for example taxol), or metabolite synthesis (for example methotrexate). An activable cytotoxic compound is typically used in the context of Photodynamic Therapy (for example photofrin), and is to be activated by an external source such as a laser source to produce its therapeutic effect. Other typical cytotoxic compounds are typically selected from chemotherapeutic agent as herein described or as known by the skilled oncologist.

A prodrug (for instance capecitabine or irinotecan) is metabolized in its active form in vivo to produce its expected therapeutic effect.

Examples of inorganic compound usable as the at least one compound of interest can be selected from a transition metal coordination complex, a radiopharmaceutical compound, a nanoparticle, etc.

Transition metal coordination complexes offer potential advantages over the more common organic-based drugs, including a wide range of coordination numbers and geometries, accessible redox states, 'tune-ability' of the thermodynamics and kinetics of ligand substitution, as well as a wide structural diversity. Metal-based substances interact with cell molecular targets, affecting biochemical functions resulting in malignant cell destruction. Transition metal coordination complexes are typically cytotoxic agents (for instance, platinum coordination complexes: cisplatin, carboplatin, oxaloplatin, or ruthenium or gold coordination complexes) acting on DNA structures.

Radiopharmaceutical compounds emit radiations for diagnosis purposes or in order to selectively destroy malignant cells. Typical radiopharmaceuticals may contain for example strontium-89, thallium-201, techtenium-99, samarium-83, etc.

Nanoparticle may be selected typically from a metal oxide nanoparticle (see WO 2009/147214 and WO 2007/118884 for example), a metallic nanoparticle (gold, platinum or silver nanoparticle for instance), a metal sulfide nanoparticle ($Bi_2S_3$ for instance), and any mixture thereof (for example a gold nanoparticle covered with hafnium oxide material). The nanoparticle is for example a nanoparticle which can be activated via an external source such as an electromagnetic radiation source, an ultrasound source, or a magnetic source, etc.

The at least one compound of interest, which is administered in combination with a biocompatible nanoparticle as described hereinabove (typically sequentially administered as herein described), may be encapsulated in a carrier or grafted (or bound) to such a carrier according to means known by the skilled person. A typical carrier is for example a liposome (such as DOXIL or ThermoDox which uses thermosensitive lipid), micelle, polymeric (or "polymer") carrier, hydrogel, gel, co-polymeric carrier, protein carrier, inorganic carrier.

The pharmaceutical composition of the invention (defined by the combination of the compound of interest and of the at least two distinct nanoparticles) can be used in many fields, particularly in human or veterinary medicine. This composition is typically for use in an animal, preferably in a mammal (for example in the context of veterinary medicine), even more preferably in a human being whatever its age or sex.

The pharmaceutical compositions of the invention can be used in cardiovascular diseases, Central Nervous System (CNS) diseases, gastrointestinal diseases, genetic disorders, hematological disorders, hormonal disorders, immunology, infectious diseases, metabolic disorders, musculoskeletal disorders, oncology, respiratory diseases, toxicology, etc. In a preferred embodiment, the pharmaceutical composition is used in cardiovascular diseases, CNS diseases, oncology, infectious diseases, and metabolic disorders.

In the context of the present invention, the at least two distinct biocompatible nanoparticles on one side and the compound(s) ("compound(s) of interest") on the other side are advantageously to be separately administered in a subject in need of said compound(s), typically with an interval of between more than 5 minutes and about 72 hours, typically between more than 5 minutes and about 24 hours, preferably between more than 5 minutes or 30 minutes and about 12 hours, in order to optimize the compound(s) pharmaceutical efficacy.

In the present invention, when the at least two distinct nanoparticles and the compound(s) ("compound(s) of interest") are advantageously to be separately administered in a subject in need of said compound(s) as explained previously, typically with an interval of between more than 5 minutes and about 72 hours, the absolute surface charge value of the "first" biocompatible nanoparticle being advantageously of at least 10 mV (|10 mV|) and the "second" biocompatible nanoparticle, or any additional biocompatible nanoparticle, having a difference of at least 10 mV with the absolute surface charge value of the "first" biocompatible nanoparticle.

In a particular embodiment of the present invention, when the at least two distinct nanoparticles and the compound(s) ("compound(s) of interest") are separately administered in a subject in need of said compound with an interval of between more than 5 minutes and about 24 hours, the nanoparticles being preferably administered before the compound(s), the absolute surface charge value of the "first" biocompatible nanoparticle is advantageously of at least 15 mV (|15 mV|).

Also herein described is a method for treating a subject suffering of a disease such as those herein mentioned, wherein said method comprises administering to said subject a pharmaceutical composition of the invention, typically administering at least two distinct biocompatible nanoparticles and at least one compound of interest as herein described. Anyone of the at least two nanoparticles or at least one compound of interest can be administered first to the subject as long as the at least two biocompatible nanoparticles on one side and the at least one compound on the other side are administered between more than 5 minutes and about 72 hours from each other. Administration of any of said at least two nanoparticles or at least one compound of interest can be a single administration of each, repeated administrations of each, for example several consecutive administrations of each. The at least two distinct biocompatible nanoparticles may be administered once and the at least one compound of interest may be administered more than once and vice versa.

In a particular embodiment, the at least two distinct biocompatibles nanoparticle are at least administered at the beginning of a protocol comprising several administrations of the at least one compound of interest, i.e. at least at the first administration of said at least one compound of interest and before or after the administration thereof.

In another particular embodiment, the at least two distinct biocompatible nanoparticles are not administered at the beginning of a protocol comprising several administrations of the at least one compound of interest and are not administered before the second or third administration of said at least one compound of interest, and before or after the administration thereof.

In the context of these last two embodiments, the at least two distinct biocompatible nanoparticles can also be administered together (before or after as previously explained) with the at least one compound of interest during part or all of the subsequent administrations of said at least one compound of interest.

In a particular embodiment, the at least two distinct nanoparticles of the invention are administered to the subject before administration to said subject of the at least one compound of interest, typically between more than 5 minutes and about 72 hours before administration of said at least one compound of interest.

The at least two distinct biocompatible nanoparticles of the pharmaceutical composition of the invention can be administered by any route such as subcutaneous, intra dermic, oral route, nasal route (inhalation), intra venous (IV), intra-arterial, and/or intra peritoneal. A preferred route of administration is the intra venous route. The at least two distinct biocompatible nanoparticles of the pharmaceutical composition of the invention can be administered by different routes simultaneously or separately.

The compound(s) of interest of the pharmaceutical composition of the invention can be administered by different routes such as subcutaneous, intra venous (IV), intra-dermic, intra-arterial, airways (inhalation), intra peritoneal, intra muscular and/or oral route (per os).

The following examples illustrate the invention without limiting its scope.

EXAMPLES

Figure 1:
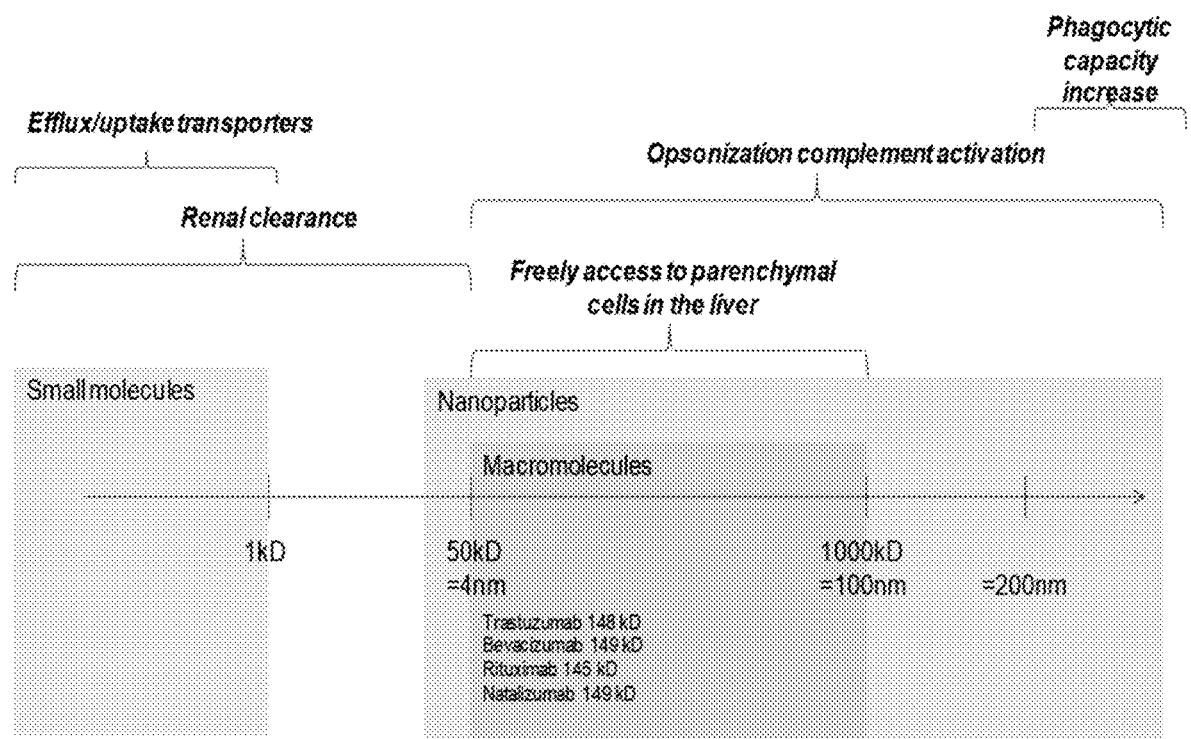
FIG. 1: Schematic view of possible routes for therapeutic compounds removal from blood circulation depending on the compound's size (longest dimension).

Example 1: Synthesis of Liposomes as the "First" and/or "Second" Biocompatible Nanoparticles Liposomes are prepared using the lipid film re-hydration method.

Synthesis of "First" and/or "Second" Biocompatible Nanoparticles with an Absolute Surface Charge Value of at Least 10 mV (|10 mV|):

a) lipids were solubilized in chloroform. Chloroform was finally evaporated under a nitrogen flow. Re-hydration of the lipid film with HEPES 20 mM and NaCl 140 mM at pH 7.4 was performed at 60° C., so that the lipid concentration was 25 mM.

The following lipid composition was used to prepare charged liposomes: DPPC (DiPalmitoylPhosphatidylCholine) 62% mol; HSPC (Hydrogenated Soybean PhosphatidylCholine) 20% mol; CHOL (Cholesterol) 16% mol; POPS (1-Palmitoyl-2-Oleoyl Phosphatidyl Serine) 1% mol; D SPE-PEG (DiStearylPhosphatidylEthanolamine-[methoxy(PolyElthyleneGlycol)-2000]) 1% mol.

b) freeze-thaw cycles were then performed 6 times, by successively plunging the sample into liquid nitrogen and into a water bath regulated at 60° C.

c) a thermobarrel extruder (LIPEX™ Extruder, Northern Lipids) was used to calibrate the size of the liposomes under controlled temperature and pressure. In all cases, extrusion was performed at 60° C. First, 5 passages through a polyethersulfone (PES) 0.45 μm pores-sized membrane were performed at a pressure of 5 bars, then 12 passages through a PES 0.22 μm pores-sized membrane at 10 bars, and finally 12 passages through a 0.1 μm polyvinylidene fluoride (PVDF) membrane at 15 bars.

Size distribution of the as-prepared liposomes was determined by dynamic light scattering (DLS) using a Zetasizer NanoZS (Malvern instrument) with a 633 nm HeNe laser at an angle of 90° C. The liposomes suspension was diluted 100 times in HEPES 20 mM and NaCl 140 mM at pH 7.4. Liposome size (i.e. hydrodynamic diameter) was equal to about 145 nm (distribution by intensity) with a polydispersity index (PDI) equal to about 0.1.

As understandable by the skilled person, the desired surface charge was obtained thanks to the selected lipidic composition, and its value was confirmed by zeta potential measurement using a Zetasizer NanoZS (Malvern instrument).

The liposomes were diluted 100 times in a sodium chloride solution at 1 mM and the pH of the resulting suspension was adjusted to pH 7.4. The liposomes surface charge was equal to about −25 mV at pH 7.4, NaCl 1 mM.

Synthesis of "Second" and/or "First" Biocompatible Nanoparticles:

a) lipids were solubilized in chloroform. Chloroform was finally evaporated under a nitrogen flow to form a lipid film on the Pyrex tube walls. Re-hydration of the lipid film with HEPES 25 mM and NaCl 150 mM at pH 7.4 was performed at 60° C., so that the lipid concentration was 50 mM.

The following lipid composition was used: DPPC (DiPalmitoylPhosphatidylCholine) 57% mol; HSPC (Hydrogenated Soybean PhosphatidylCholine) 21% mol; CHOL (Cholesterol) 16% mol; POPS (1-Palmitoyl-2-Oleoyl Phosphatidyl Serine) 5% mol; DSPE-PEG (DiStearylPhosphatidylEthanolamine-[methoxy(PolyElthyleneGlycol)-2000]) 1% mol.

b) freeze-thaw cycles were then performed 6 times, by successively plunging the sample into liquid nitrogen and into a water bath regulated at 60° C.

c) the liposomes solution was then ultra-sonicated with a probe at a power of 230 W during 30s.

d) a thermobarrel extruder (LIPEX™ Extruder, Northern Lipids) was used to calibrate the size of the liposomes under controlled temperature and pressure. Extrusion was performed at 60° C. First, 10 passages were applied through a 0.1 μm pores size polyvinylidene fluoride (PVDF) membrane under a pressure of 10 bars, then 10 passages through a 0.08 μm pores size polycarbonate (PC) membrane under a pressure of 15 bars, and finally 10 passages through a 0.05 μm pores size PC membrane under a pressure of 20 bars.

e) the liposomes solution was then concentrated twice by membrane ultrafiltration on Vivaspin concentrators, with polyethylene sulfone (PES) membrane with a cut-off 300 KDa.

Size distribution of the as-prepared liposomes was determined by dynamic light scattering (DLS) using a Zetasizer NanoZS (Malvern instrument) with a 633 nm HeNe laser at an angle of 173° C. The liposomes solution was diluted 200 times in HEPES 25 mM and NaCl 150 mM at pH 7.4. Liposomes size (i.e. hydrodynamic diameter) was equal to about 70 nm (distribution by intensity) with a polydispersity index (PdI) equal to about 0.1.

The surface charge of the liposomes was determined by zeta potential measurement using a Zetasizer NanoZS (Malvern instrument). The liposomes solution was diluted 200 times in a sodium chloride solution at 1 mM and the pH of the solution was adjusted to pH 7. The liposomes surface charge was equal to about −40 mV at pH 7, NaCl 1 mM.

Example 2: Synthesis of Liposomes as the "First" and/or "Second" Biocompatible Nanoparticles Liposomes are prepared using the lipid film re-hydration method.

—Synthesis of "First" and/or "Second" Biocompatible Nanoparticles with Absolute Surface Charge Value of at Least 10 mV (|10 mV|):

a) lipids were solubilized in chloroform. Chloroform is finally evaporated under a nitrogen flow to form a lipid film on the Pyrex tube walls. Re-hydration of the lipid film with HEPES 25 mM and NaCl 150 mM at pH 7.4 is performed at 60° C., so that the lipid concentration is 50 mM.

The following lipid composition is used: HSPC (Hydrogenated Soybean PhosphatidylCholine) 59% mol; CHOL (Cholesterol) 38% mol; DSPE-PEG (DiStearylPhosphatidylEthanolamine-[methoxy(PolyElthyleneGlycol)-2000]) 3% mol.

b) freeze-thaw cycles were then performed 6 times, by successively plunging the sample into liquid nitrogen and into a water bath regulated at 60° C.

c) the liposomes solution was then ultra-sonicated with a probe at a power of 230 W during 30s.

d) a thermobarrel extruder (LIPEX™ Extruder, Northern Lipids) was used to calibrate the size of the liposomes under controlled temperature and pressure. Extrusion was performed at 60° C. First, 10 passages were applied through a 0.1 μm pores size polyvinylidene fluoride (PVDF) membrane under a pressure of 15 bars, then 18 passages through a 0.08 μm pores size polycarbonate (PC) membrane under a pressure of 20 bars.

e) the liposomes solution was then concentrated twice by membrane ultrafiltration on Vivaspin concentrators, with polyethylene sulfone (PES) membrane with a cut-off 300 KDa.

Size distribution of the as-prepared liposomes was determined by DLS using a Zetasizer NanoZS (Malvern instrument) with a 633 nm HeNe laser at an angle of 173° C. The liposomes solution was diluted 200 times in HEPES 25 mM and NaCl 150 mM at pH 7.4. Liposomes size (i.e. hydrodynamic diameter) was equal to about 90 nm (distribution by intensity) with a polydispersity index (PdI) equal to about 0.1.

The surface charge of the liposomes was determined by zeta potential measurement using a Zetasizer NanoZS (Malvern instrument). The liposomes solution was diluted 200 times in a sodium chloride solution at 1 mM and the pH of the solution was adjusted to pH 7. The liposomes surface charge was equal to about −25 mV at pH 7, NaCl 1 mM.

The final lipid concentration of the liposomes solution was measured by a colorimetric assay: phospholipase D cuts the phosphaticylcholine molecules, thus relieving the choline group which is going to form a blue pigment by reacting with the chromogenic substrate. Lipids concentration was found at 100 mM.

—Synthesis of "Second" and/or "First" Biocompatible Nanoparticles:

a) lipids were solubilized in chloroform. Chloroform was finally evaporated under a nitrogen flow to form a lipid film on the Pyrex tube walls. Re-hydration of the lipid film with HEPES 25 mM and NaCl 150 mM at pH 7.4 was performed at 60° C., so that the lipid concentration is 50 mM.

The following lipid composition was used: DPPC (DiPalmitoylPhosphatidylCholine) 57% mol; HSPC (Hydrogenated Soybean PhosphatidylCholine) 21% mol; CHOL (Cholesterol) 16% mol; POPS (1-Palmitoyl-2-Oleoyl Phosphatidyl Serine) 5% mol; DSPE-PEG (DiStearylPhosphatidylEthanolamine-[methoxy(PolyElthyleneGlycol)-2000]) 1% mol.

b) freeze-thaw cycles were then performed 6 times, by successively plunging the sample into liquid nitrogen and into a water bath regulated at 60° C.

c) a thermobarrel extruder (LIPEX™ Extruder, Northern Lipids) was used to calibrate the size of the liposomes under controlled temperature and pressure. Extrusion was performed at 60° C. First, 5 passages through a polyethersulfone (PES) 0.45 µm pores-sized membrane were performed at a pressure of 5 bars, then 12 passages through a PES 0.22 µm pores-sized membrane at 10 bars, and finally 12 passages through a 0.1 µm polyvinylidene fluoride (PVDF) membrane at 15 bars.

d) the liposomes solution was then concentrated twice by membrane ultrafiltration on Vivaspin concentrators, with polyethylene sulfone (PES) membrane with a cut-off 300 KDa.

Size distribution of the as-prepared liposomes was determined by dynamic light scattering (DLS) using a Zetasizer NanoZS (Malvern instrument) with a 633 nm HeNe laser at an angle of 173° C. The liposomes solution was diluted 200 times in HEPES 25 mM and NaCl 150 mM at pH 7.4. Liposomes size (i.e. hydrodynamic diameter) was equal to about 145 nm (distribution by intensity) with a polydispersity index (PdI) equal to about 0.1.

The surface charge of the liposomes was determined by zeta potential measurement using a Zetasizer NanoZS (Malvern instrument). The liposomes solution was diluted 200 times in a sodium chloride solution at 1 mM and the pH of the solution was adjusted to pH 7. The liposomes surface charge was equal to about −40 mV at pH 7, NaCl 1 mM.

The final lipid concentration of the liposomes solution was measured by a colorimetric assay: phospholipase D cuts the phosphaticylcholine molecules, thus relieving the choline group which is going to form a blue pigment by reacting with the chromogenic substrate. Lipids concentration was found at 100 mM.

Figure 2:
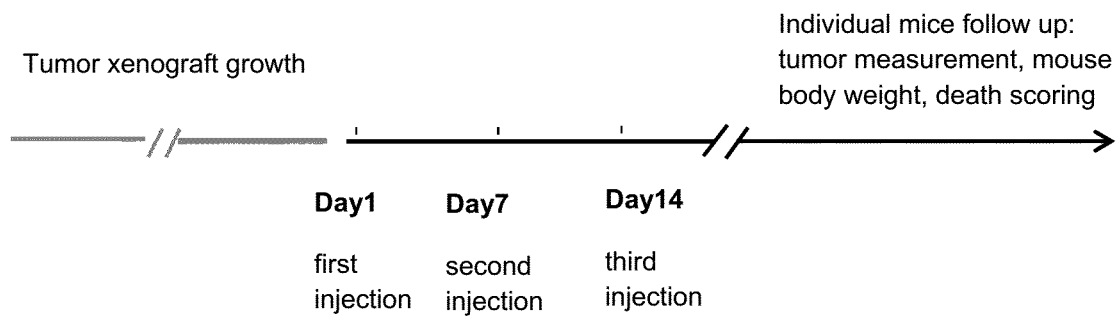
FIG. 2: Schematic representation of the treatment schedule for the pharmaceutical composition comprising (i) the at least two biocompatible nanoparticles of example 2 and (ii) the Dox-NP® in MDA-MB-23 1-lucD3H2LN xenografts.
Figure 3:
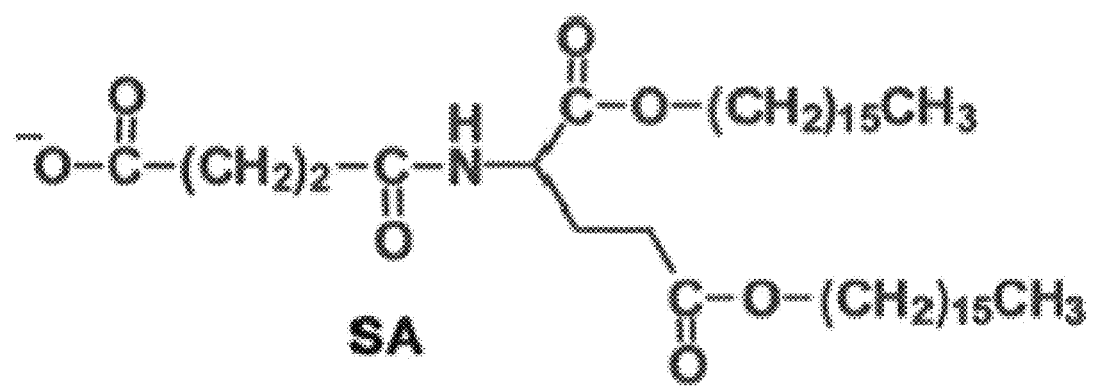
FIG. 3: Chemical formula of L-Glutamic acid, N-(3-carboxy-1-oxopropyl)-, 1,5-dihexadecyl ester (SA-lipid).

Example 3: Method for the Evaluation of the Efficacy and Toxicity of a Pharmaceutical Composition Comprising the at Least Two Biocompatible Nanoparticles Suspensions of Example 2 and the Dox-NP® in MDA-MB-231-lucD3H2LN Xenografts (Cf. FIG. 2)

The pharmaceutical composition comprising (i) the at least two distinct "first" and "second" biocompatible nanoparticles from example 2 and (ii) Dox-NP® (Liposomal Encapsulated Doxorubicin) as the therapeutic compound of interest, is administered in nude mice bearing MDA-MB-231-lucD3H2LN xenografted tumor in the following manner:

a) the Dox-NP® and the biocompatible nanoparticles from example 2 are administered by intravenous injection (IV) via lateral tail vein.

The Dox-NP® (Avanti Polar lipids—Liposomal formulation of 2 mg/ml doxorubicin HCl at pH 6.5-6.8, in 10 mM histidine buffer, with 10% w/v sucrose) are injected without additional dilution at the volume required to obtain 3 mg/kg of injected doxorubicin.

The biocompatible nanoparticles suspensions from example 2 are used without any additional dilution.

b) four groups of mice are treated as illustrated on FIG. 2:

—Group 1: sterile glucose 5% (control (vehicle) group). Mice are intravenously (IV) injected with a sterile glucose 5% solution on day 1, day 7 and day 14.

—Group 2: "First" and "second" biocompatible nanoparticles from example 2 (control group).

Mice are intravenously (IV) injected with the "first" and "second" biocompatible nanoparticles from example 2 (10 ml/kg) on day 1, day 7 and day 14. Each time (day), the injection of the first biocompatible nanoparticles is performed 4 hours before injection of the second biocompatible nanoparticles.

—Group 3: Dox-NP® (3 mg/kg doxorubicin) (treatment group).

Mice are intravenously (IV) injected with Dox-NP® (3 mg/kg doxorubicin) on day 1, day 7 and day 14.

—Group 4: pharmaceutical composition, i.e. the combination of (i) the at least two distinct ("first" and "second") biocompatible nanoparticles from example 2 and of (ii) Dox-NP® (3 mg/kg doxorubicin) (treatment group).

Mice are intravenously (IV) injected with the biocompatible nanoparticles from example 2 (10 ml/kg) and with the Dox-NP® (3 mg/kg doxorubicin) on day 1, day 7 and day 14. Each time (day), the simultaneous injection of the "first" and "second" biocompatible nanoparticles from example 2 is performed 4 hours before the injection of Dox-NP® (3 mg/kg doxorubicin).

—Group 5: pharmaceutical composition, i.e. the combination of (i) the at least two distinct biocompatible nanoparticles from example 2 and of (ii) Dox-NP® (3 mg/kg doxorubicin) (treatment group).

Mice are intravenously (IV) injected with the biocompatible nanoparticles from example 2 (10 ml/kg) and with the Dox-NP® (3 mg/kg doxorubicin) on day 1, day 7 and day 14. Each time (day), the injection of the "first" and "second" biocompatible nanoparticles from example 2 is performed 4 hours and 1 hours respectively before the injection of Dox-NP® (3 mg/kg doxorubicin).

c) any clinical sign of toxicity is assessed after the administration of the pharmaceutical composition; and d) the tumor volume is measured from two dimensional tumor volume measurements with a digital caliper using the following formula:

$$\text{Tumor volume (mm}^3) = \frac{\text{length (mm)} \times (\text{width})^2 (\text{mm}^2)}{2}$$

Example 4: Synthesis of Liposomes as the "First" or "Second" Biocompatible Nanoparticles Liposomes are prepared using the lipid film re-hydration method:

a) Lipids are solubilized in chloroform. Chloroform is finally evaporated under a nitrogen flow to form a lipid film on the Pyrex tube walls. Re-hydration of the lipid film with HEPES 25 mM and NaCl 150 mM at pH 7.4 is performed at 60° C., so that the lipid concentration is 50 mM.

The following lipid composition was used to prepare charged liposomes: DPPC (DiPalmitoylPhosphatidylCholine) 58% mol; HSPC (Hydrogenated Soybean PhosphatidylCholine) 21% mol; CHOL (Cholesterol) 16% mol; POPS (1-Palmitoyl-2-Oleoyl PhosphatidylSerine) 5% mol.

b) Freeze-thaw cycles are then performed 6 times, by successively plunging the sample into liquid nitrogen and into a water bath regulated at 60° C. Ultra-sonication of the liposomes solution is performed during 30s every 3 freeze-thaw cycles and just before extrusion.

c) A thermobarrel extruder (LIPEX™ Extruder, Northern Lipids) is used to calibrate the size of the liposomes under controlled temperature and pressure. Extrusion is performed at 60° C. Ten passages are applied through a 0.1 µm pores size polyvinylidene fluoride (PVDF) membrane under a pressure of 10 bars.

Size distribution of the as-prepared liposomes is determined by dynamic light scattering (DLS) using a Zetasizer NanoZS (Malvern instrument) with a 633 nm HeNe laser at an angle of 173° C. The liposomes solution is diluted 200 times in HEPES 25 mM and NaCl 150 mM at pH 7.4. Liposomes size (i.e. hydrodynamic diameter) is equal to about 170 nm (distribution by intensity) with a polydispersity index (PdI) equal to about 0.2.

As understandable by the skilled person, the desired surface charge is obtained thanks to the selected lipid composition, and its value is confirmed by zeta potential measurement using a Zetasizer NanoZS (Malvern instrument). The liposomes are diluted 200 times in a sodium chloride solution at 1 mM and the pH of the solution is adjusted to pH 7. The liposomes surface charge is equal to about −40 mV at pH 7, NaCl 1 mM.

The final lipid concentration of the liposomes solution is measured by a colorimetric assay (Bartlett method). The method is based on total phosphorus determination through an acidic digestion of phospholipid. The released inorganic phosphate is reacted with ammonium molybdate, the complex giving a strong blue color. Lipids concentration is equal to about 50 mM.

Example 5: Synthesis of Liposomes as the "First" or "Second" Biocompatible Nanoparticles Liposomes are prepared using the lipid film re-hydration method:

a) Lipids are solubilized in chloroform. Chloroform is finally evaporated under a nitrogen flow to form a lipid film on the Pyrex tube walls. Re-hydration of the lipid film with HEPES 25 mM and NaCl 150 mM at pH 7.4 is performed at 60° C., so that the lipid concentration is 50 mM.

The following lipid composition was used to prepare the charged liposomes: DPPC (DiPalmitoylPhosphatidylCholine) 45.15% mol; CHOL (Cholesterol) 45.15% mol; DSPE-PEG (DiStearylPhosphatidylEthanolamine-[methoxy(PolyElthyleneGlycol)-2000]) 0.60% mol; L-Glutamic acid, N-(3-carboxy-1-oxopropyl)-, 1,5-dihexadecyl ester (SA-lipid) 9.10% mol. The SA-lipid brings COOH groups on the liposomes surface.

b) Freeze-thaw cycles are then performed 6 times, by successively plunging the sample into liquid nitrogen and into a water bath regulated at 60° C.

c) A thermobarrel extruder (LIPEX™ Extruder, Northern Lipids) is used to calibrate the size of the liposomes under controlled temperature and pressure. Extrusion is performed at 60° C. Seven passages are applied through a 0.45 µm pores size polyvinylidene fluoride (PVDF) membrane under a pressure of 3 bars and ten passages through a 0.22 µm pores size polyvinylidene fluoride (PVDF) membrane under a pressure of 10 bars. Size distribution of the as-prepared liposomes is determined by dynamic light scattering (DLS) using a Zetasizer NanoZS (Malvern instrument) with a 633 nm HeNe laser at an angle of 173° C. The liposomes solution is diluted 200 times in HEPES 25 mM and NaCl 150 mM at pH 7.4. Liposomes size (i.e. hydrodynamic diameter) is equal to about 230 nm (distribution by intensity) with a polydispersity index (PdI) equal to about 0.2.

As understandable by the skilled person, the desired surface charge is obtained thanks to the selected lipid composition, and its value is confirmed by zeta potential measurement using a Zetasizer NanoZS (Malvern instrument). The liposomes solution is diluted 200 times in a sodium chloride solution at 1 mM and the pH of the solution is adjusted to pH 7. The liposomes surface charge is equal to about −60 mV at pH 7, NaCl 1 mM.

The final lipid concentration of the liposomes solution is measured by a colorimetric assay (Bartlett method). The method is based on total phosphorus determination through an acidic digestion of phospholipid. The released inorganic phosphate is reacted with ammonium molybdate and the complex giving a strong blue color. Lipids concentration is equal to about 50 mM.

Example 6: Synthesis of Liposomes as the "First" or "Second" Biocompatible Nanoparticles Liposomes are prepared using the lipid film re-hydration method:

a) Lipids are solubilized in chloroform. Chloroform is finally evaporated under a nitrogen flow to form a lipid film on the Pyrex tube walls. Re-hydration of the lipid film with HEPES 25 mM and NaCl 150 mM at pH 7.4 is performed at 60° C. and the lipid concentration is 50 mM. The following lipid composition was used to prepare the charge liposomes: DSPC (1,2-distearoyl-sn-glycero-3-phosphocholine) 60% mol, CHOL (Cholesterol) 35% mol; and Succinyl PE (1,2-dioleoyl-sn-glycero-3-phosphoethanolamine-N-succinyl) 5% mol.

b) Freeze-thaw cycles are then performed 6 times, by successively plunging the sample into liquid nitrogen and into a water bath regulated at 60° C. Ultra-sonication of the liposomes solution is performed during 30s, every 3 freeze-thaw cycles and just before extrusion.

c) A thermobarrel extruder (LIPEX™ Extruder, Northern Lipids) is used to calibrate the size of the liposomes under controlled temperature and pressure. Extrusion is performed at 60° C. Twelve passages are applied through a 0.22 μm pores size polyvinylidene fluoride (PVDF) membrane under a pressure of 12 bars.

d) Conjugation of p-aminophenyl-α-D-mannopyranoside (MAN) to Succinyl PE liposome: The succinyl PE liposome surface are modified with a mannose derived ligand p-aminophenyl-α-D-mannopyranoside (MAN), using carbodiimide coupling to develop mannose conjugated liposome. MAN is covalently coupled by its amino group to the carboxylic acid group of Succinyl PE, present on the surface of preformed Succinyl PE liposome. Briefly, to the preformed Succinyl PE liposome solution are added EDC (1-ethyl-3-[3-dimethylaminopropyl] carbodiimide hydrochloride), (Succinyl PE/EDC 1:10 molar ratio) and N-hydroxysuccinimide (NHS) (NHS/EDC 1:2.5 molar ratio). The pH of the suspension is then adjusted at 6 with NaOH 1M and the resulting suspension is stirred for 15 minutes at room temperature. Subsequently, the pH of the solution is adjusted at 7 with NaOH 1M and the aqueous MAN solution is added (Succinyl PE/MAN 1:2 molar ratio) to the solution. pH is readjusted at 7 using NaOH 1M and the suspension is stirred for 2 additional hours at room temperature. Excessive unbound MAN, EDC and NHS molecules are removed by 3 steps of dialysis with dilution factor (×500; ×500; ×500) using a 50 KDa cellulose membrane.

Of note, due to possible dilution upon dialysis, the liposomes solution can be concentrated by centrifugation (typically a Sigma 3-15K centrifuge at 5° C.; 1,200 rpm) using membrane ultrafiltration on Vivaspin concentrators with a polyethylene sulfone (PES) membrane and a cut-off 300 KDa.

Size distribution of the as-prepared liposomes is determined by dynamic light scattering (DLS) using a Zetasizer NanoZS (Malvern instrument) with a 633 nm HeNe laser at an angle of 173° C. The liposomes solution is diluted 200 times in HEPES 25 mM and NaCl 150 mM at pH 7.4. Liposomes size (i.e. hydrodynamic diameter) is about 230 nm (distribution by intensity) with a polydispersity index (PDI) around 0.2.

As understandable by the skilled person, the desired surface charge is obtained thanks to the selected lipid composition, and its value is confirmed by zeta potential measurement using a Zetasizer NanoZS (Malvern instrument). The liposomes solution is diluted 200 times in a sodium chloride solution at 1 mM and at pH 7. The liposomes surface charge is around −70 mV at NaCl 1 mM, pH 7.

The final lipid concentration of the liposomes solution is measured by a colorimetric assay (Bartlett method). The method is based on total phosphorus determination through an acidic digestion of phospholipid. The released inorganic phosphate is reacted with ammonium molybdate and the complex giving a strong blue color. Lipids concentration is equal to about 50 mM.

We claim:

1. A method of treating a subject having a disease comprising a step of administering at least one pharmaceutical compound to a subject in need thereof and a distinct step of administering at least two distinct biocompatible nanoparticles to said subject, wherein the longest dimension of each of the at least two biocompatible nanoparticles is between about 4 nm and about 500 nm, the surface charge value of a first biocompatible nanoparticle is a negative charge below −10 mV, the surface charge value of a second biocompatible nanoparticle, or of any additional biocompatible nanoparticle, is negative and has a difference of at least 10 mV to the negative surface charge value of the first biocompatible nanoparticle, each of the at least two biocompatible nanoparticles is not used as the at least one pharmaceutical compound, and said at least two distinct biocompatible nanoparticles are administered to the subject separately from the at least one pharmaceutical compound between 5 minutes and about 24 hours before said at least one pharmaceutical compound.

2. The method according to claim 1, wherein the at least two distinct biocompatible nanoparticles are administered separately from each other to the subject in need of treatment with said pharmaceutical compound.

3. The method according to claim 1, wherein the at least two distinct nanoparticles are organic nanoparticles.

4. The method according to claim 3, wherein the at least two distinct nanoparticles are selected from lipid-based nanoparticles, protein-based nanoparticles, polymer-based nanoparticles, co-polymer-based nanoparticles, carbon-based nanoparticles, virus-like nanoparticles and any mixture thereof.

5. The method according to claim 1, wherein the at least two distinct nanoparticles are inorganic nanoparticles and the longest dimension of each of said nanoparticles is below about 7 nm.

6. The method according to claim 1, wherein the at least two nanoparticles are inorganic nanoparticles, the longest dimension of each of said nanoparticles is of at least 10 nm, and the inorganic material of each of the nanoparticles is selected from (i) one or more divalent metallic elements, (ii) one or more trivalent metallic elements, and (iii) one or more tetravalent metallic elements comprising Si.

7. The method according to claim 6, wherein the inorganic material is selected from calcium carbonate ($CaCO_3$), magnesium carbonate ($MgCO_3$), magnesium hydroxide ($Mg(OH)_2$), iron hydroxide ($Fe(OH)_2$), iron oxyhydroxide (FeOOH), iron(II, III) oxide ($Fe_3O_4$), iron(III) oxide ($Fe_2O_3$), aluminium oxide ($Al_3O_4$), aluminium hydroxide ($Al(OH)_3$), aluminium oxyhydroxide (AlOOH) and silicium oxide ($SiO_2$).

8. The method according to claim 1, wherein both organic and inorganic nanoparticles are administered to the subject.

9. The method according to claim 1, wherein each of the at least two nanoparticles is further covered with a biocompatible coating.

10. The method according to claim 1, wherein the administration of the at least two biocompatible nanoparticles and of the at least one pharmaceutical compound maintains the therapeutic benefit of said at least one pharmaceutical compound and reduces toxicity, or increases the therapeutic benefit of said at least one pharmaceutical compound for an equivalent or reduced toxicity, for the subject, when compared to therapeutic benefit and toxicity induced by the standard therapeutic dose(s) of said at least one pharmaceutical compound.

11. The method according to claim 1, wherein the administration of the at least two biocompatible nanoparticles and of the at least one pharmaceutical compound allows a reduction of at least 10% of the administered at least one pharmaceutical compound therapeutic dose when compared to the standard therapeutic dose of said at least one pharmaceutical compound while maintaining the same therapeutic benefit for an equivalent toxicity or a reduced toxicity for the subject or while increasing the therapeutic benefit for an equivalent or reduced toxicity for the subject.

12. The method according to claim 1, wherein the at least two nanoparticles are cleared from the subject to whom it has been administered within one hour and six weeks after their administration to said subject.

13. The method according to claim 1, wherein the at least one pharmaceutical compound is an organic compound selected from a biological compound, a small molecule targeted therapeutic, an oncolytic virus and a cytotoxic compound.

14. The method according to claim 13, wherein the at least one pharmaceutical compound is selected from an antibody, an oligonucleotide, and a synthesized peptide.

15. The method according to claim 1, wherein the at least one pharmaceutical compound is an inorganic compound selected from a metallic nanoparticle, a metal oxide nanoparticle, a metal sulfide nanoparticle, and any mixture thereof.

16. The method according to claim 1, wherein the at least one pharmaceutical compound is encapsulated in, or bound to, a carrier.

17. The method according to claim 6, wherein said one or more divalent metallic elements, are selected from Mg, Ca, Ba and Sr and said one or more trivalent metallic elements are selected from Fe and Al.

18. The method according to claim 1, wherein the disease is selected from cardiovascular diseases, Central Nervous System (CNS) diseases, gastrointestinal diseases, genetic disorders, hematological disorders, hormonal disorders, immunology, infectious diseases, metabolic disorders, musculoskeletal disorders, oncology, respiratory diseases and toxicology.

19. The method according to claim 1, wherein the at least two distinct biocompatible nanoparticles are administered simultaneously to the subject in need of treatment with said pharmaceutical compound.

* * * * *

UNITED STATES PATENT AND TRADEMARK OFFICE
CERTIFICATE OF CORRECTION

PATENT NO. : 11,471,410 B2
APPLICATION NO. : 16/550342
DATED : October 18, 2022
INVENTOR(S) : Matthieu Germain et al.

Page 1 of 1

It is certified that error appears in the above-identified patent and that said Letters Patent is hereby corrected as shown below:

In the Specification

Column 2,
Line 62, "110:31-59" should read --11(1):31-59--.

Column 3,
Line 37, "imaging (MM)," should read --imaging (MRI),--.

Signed and Sealed this
Fifteenth Day of August, 2023

Katherine Kelly Vidal
*Director of the United States Patent and Trademark Office*